United States Patent [19]

Campaigne et al.

[11] 4,254,259

[45] Mar. 3, 1981

[54] 2-AMINO-5-ETHYLOVALYL-6H-1,3,4-THIADIAZINE OXIME

[75] Inventors: Ernest E. Campaigne; Thomas Selby, both of Bloomington, Ind.

[73] Assignee: Indiana University Foundation, Bloomington, Ind.

[21] Appl. No.: 957,310

[22] Filed: Nov. 2, 1978

[51] Int. Cl.³ .................. C07D 285/16; C07D 277/30
[52] U.S. Cl. ........................... 544/8; 71/90; 548/154; 548/191; 548/196
[58] Field of Search ............................................ 544/8

[56] References Cited

U.S. PATENT DOCUMENTS 3,862,183   1/1975   Doyle, Jr. ............................... 544/8

OTHER PUBLICATIONS

Campaigne et al., Abstract of paper presented at 29th Annual Southeast Regional Meeting of the American Chemical Society in Tampa, Florida.
Campaigne et al., *J. Heterocyclic Chem.*, 15, 401(1978).
Beyer, *Quart. Rep. on Sulfur Chem.*, 5177(1970).
Elderfield, "Heterocyclic Compounds", vol. 7, pp. 826–828 (1961).
Elderfield, "Heterocyclic Compounds", vol. 5, pp. 578–579, 626–627 (1957).
Burger et al., J. Org. Chem., 12, 342 (1947).
Bose, Quart. J. Indian Chem. Soc., 1, 51 (1924).
Hamel, Bull. Soc. Chim. 29, 390 (1921).

*Primary Examiner*—Dolph H. Torrence
*Attorney, Agent, or Firm*—Kirkland & Ellis

[57]   ABSTRACT

By varying the acidity, solvent polarity, and temperature of the reaction of thiosemicarbazide with ethyl 4-chloroacetoacetate, ethyl 2-amino-6H-1,3,4-thiadiazine-5-acetate hydrochloride, ethyl 2-hydrazinothiazole-4-acetate, and ethyl 2-imino-3-aminothiazoline-4-acetate hydrochloride may be prepared selectively. Further derivatives may be prepared by benzoylation and nitrosation. These compounds have demonstrated utilities as herbicides.

1 Claim, 3 Drawing Figures

SCHEME 1
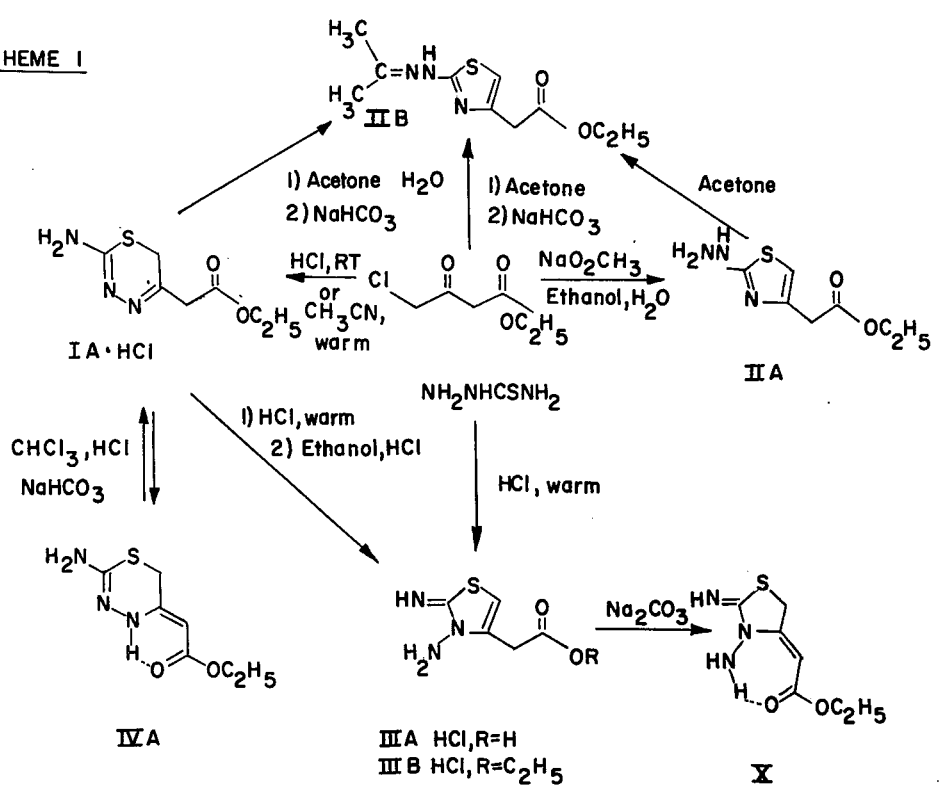
SCHEME 2
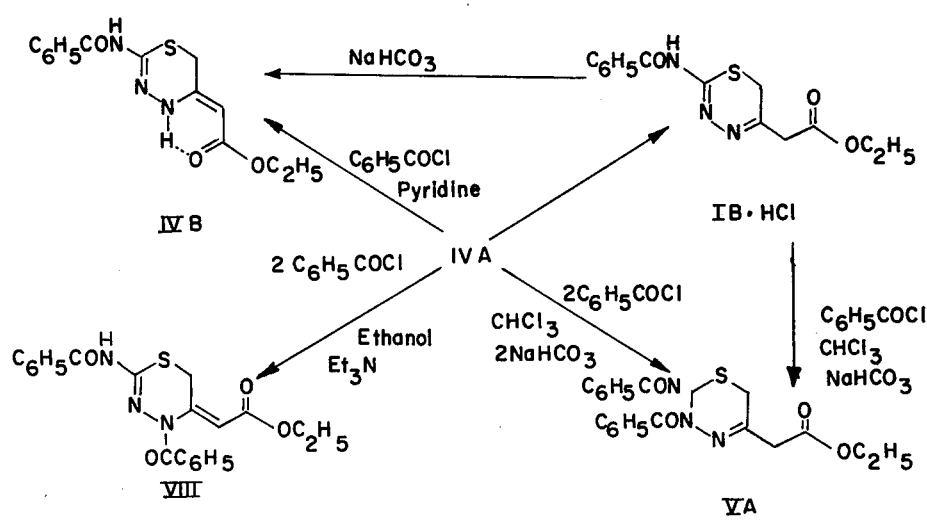

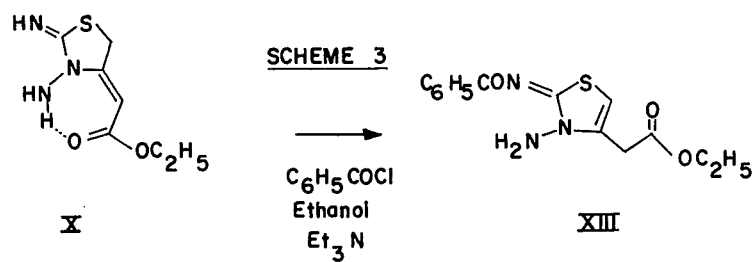

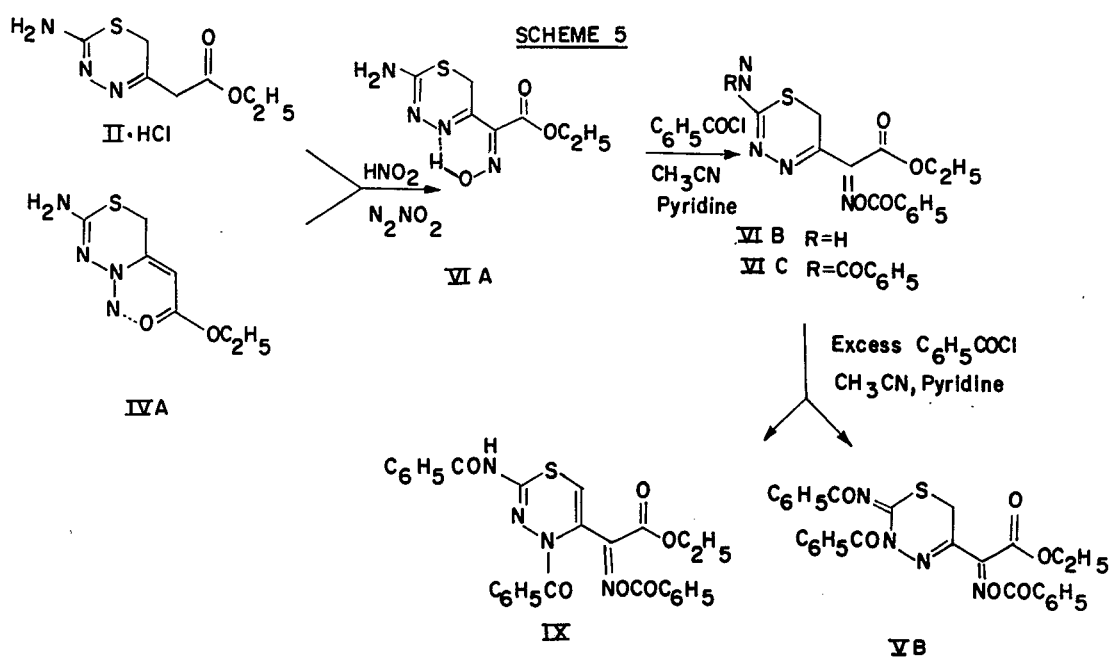
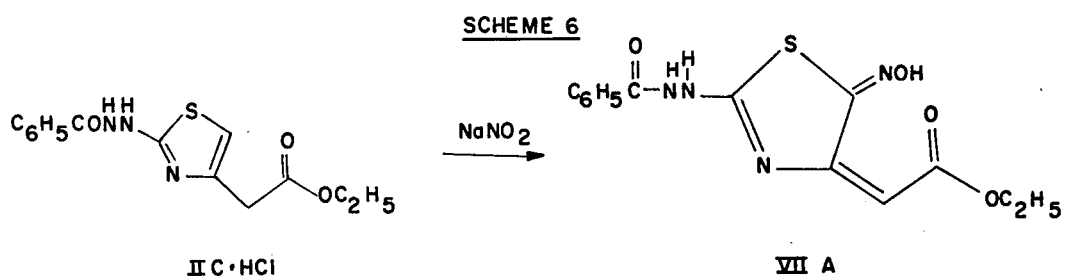
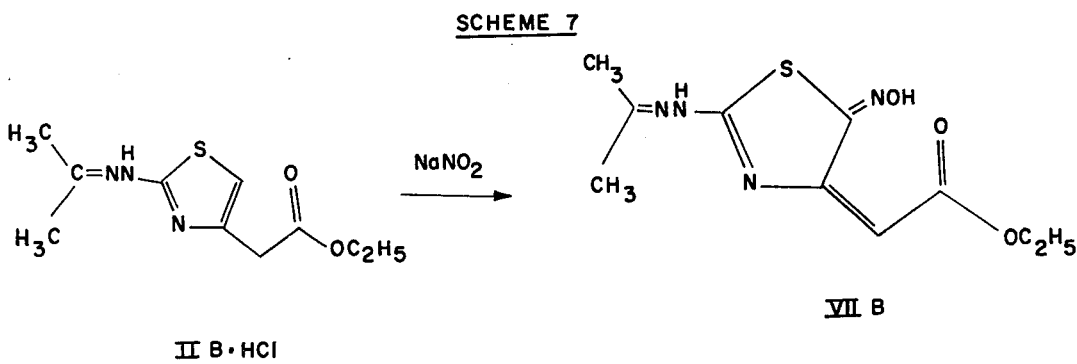

2-AMINO-5-ETHYLOVALYL-6H-1,3,4-THIADIAZINE OXIME

BACKGROUND OF THE INVENTION

1. Field of the Invention

This application relates to heterocyclic compounds and more particularly to herbicidally active substituted thiadiazine-5-,thiazole-4-, and thiazoline-4-acetic acid derivatives obtained from the reaction of ethyl 4-chloroacetoacetate with thiosemicarbazide.

2. Description of the Prior Art

Thiosemicarbazide has previously been condensed with alpha-halocarbonyl compounds resulting in the formation of a variety of five and six member heterocyclic isomers. Thus, the reaction of phenacyl bromide or chloroacetone has been disclosed to produce a thiazole, a thiazoline, or a thiadiazine. However, it has been extremely difficult to characterize the structures that are produced.

Although the prior art is aware of the reaction of such alpha halogen carbonyls with thiosemicarbzide, its reaction with gamma—halogencarbonyls is unknown although the reaction of gamma—haloketo esters with thiourea has been disclosed to yield ethyl 2-aminothiazole-4-acetate, a compound of no disclosed utility.

The prior art has thus not taught the condensation of thiosemicarbazide with ethyl-4-chloroacetoacetate much less that the products of such reaction include a wide variety of different compounds and ring configurations having selective utilities or that reaction control and direction may be exerted by the reaction solvents and conditions employed. Moreover, the prior art has not taught the preparation of derivatives of these materials by benzoylation and or nitrosation to obtain ring rearrangements and exocyclic double bonds yielding still further novel herbicidal compounds.

Accordingly, a primary object of this invention is to obtain new heterocyclic condensation products of thiosemicarbazide and ethyl 4-chloroacetoacetate under varying conditions of acidity, solvent polarity and temperature.

Another object is to obtain further active materials by selectively neutralizing, dehydrating, benzoylating, and/or nitrosating the condensation products of the character described.

SUMMARY OF THE INVENTION

The foregoing and other objects advantages and features of this invention may be achieved by condensing ethyl 4-chloroacetoacetate with thiosemicarbazide to produce a new family of heterocyclic compounds, which may in turn be further derivatized. The products of this invention include the following compounds:

(a) ethyl 6H-1,3,4-thiadiazine-5-acetates of the formula (I) and acid addition salts thereof where R is $NH_2$ or $C_6H_5CONH$;

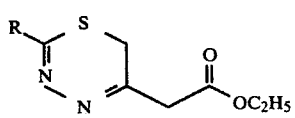
(I)

(b) 2-substituted thiazole-4-acetates of the formula (II) and acid addition salts thereof

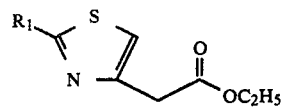
(II)

where $R_1$ is $NH_2NH$, $(CH_3)_2$=NNH, $C_6H_5CONHNH$, or $C_6H_5CH$=NNH;

(c) 2-imino-3-aminothiazoline-4-acetic acid derivatives of the formula (III) and acid addition salts thereof

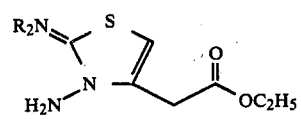
(III)

where $R_2$ is H or $C_2H_5$;

(d) 5-carbethoxymethylidene-4,5-dihydro-6H-1,3,4-thiadiazines of the formula (IV)

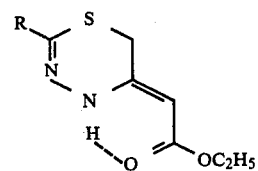
(IV)

where R is $NH_2$ or $C_6H_5$-CONH;

(e) 2-benzimido-3-benzoyl-2, 3-dihydro-6H-1,3,4-thiadizine derivatives of the formula (V)

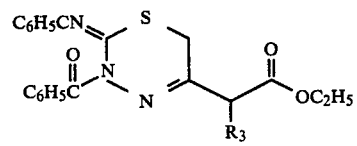
(V)

where $R_3$ is $H_2$ or

(f) 5-ethyloxalyl-6H-1,3,4-thiadiazine derivatives of the formula (VI)

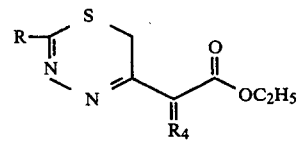
(VI)

where R is $NH_2$ or $C_6H_5CONH$ and $R_4$ is NOH or $C_6H_5COON$;

(g) 4,5-dihydro-4-carbethoxymethylidenethiazoline-5-oximes of the formula

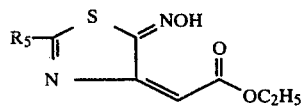
(VII)

where $R_5$ is $C_6H_5CONHNH$ or $(CH_3)_2$ C=NNH;

(h) 2-benzamido-4-benzoyl-5-carbethoxymethylidene-4,5-dihydro-6H-1,3,4-thiadiazine of the formula (VIII)

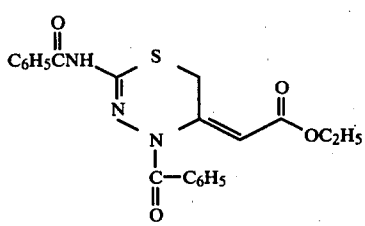

(i) 2-benzamido-4-benzoyl-5-ethyloxalyl-4H-1,3,4 thiadiazine oxime benzoate of the formula (IX)

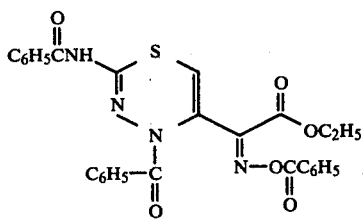

(j) 2-imino-3-amino-4-carbethoxymethylidene-thiazolidine of the formula (X)

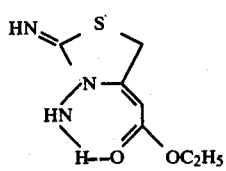

(k) ethyl 3-phenylthiazolo-[3,2-b]-s-triazole-5-acetate of the formula (XI)

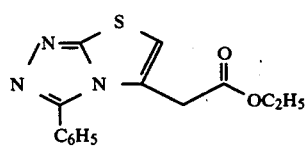

(l) ethyl-2-phenylthiazolo-[2,3-c]-s-triazole-5 acetate of the formula (XII)

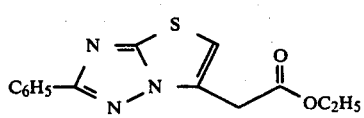

(m) ethyl 2-benzimido-3-aminothiazoline-4-acetate of the formula (XIII)

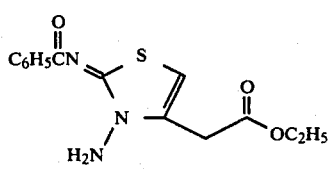

More particularly, compounds of formula (I) include the hydrochlorides of ethyl 2-amino-6H-1,3,4-thiadiazine-5-acetate (Compound IA)

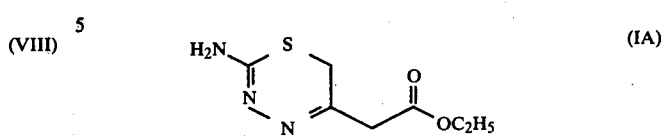

and ethyl 2-benzamido-6H-1,3,4-thiadiazine-5-acetate (Compound IB)

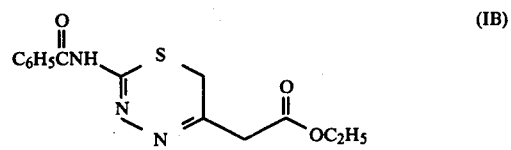

Compounds of formula (II) include ethyl 2-hydrazinothiazole-4-acetate (Compound IIA)

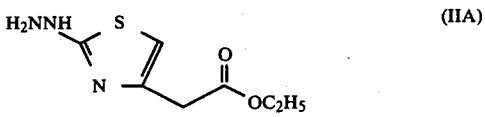

ethyl 2-isopropylidenehydrazonothiazole-4-acetate (Compound IIB)

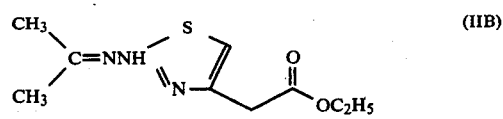

ethyl 2-(2-benzoylhydrazino)-thiazole-4-acetate (Compound IIC)

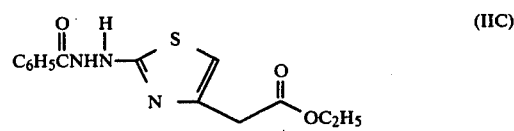

and ethyl 2-benzylidenehydrazonothiazole-4-acetate (Compound IID)

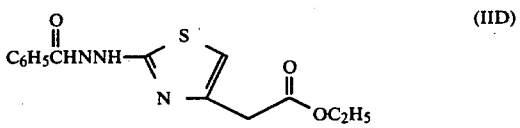

Compounds of formula (III) include the hydrochlorides of 2-imino-3-aminothiazoline-4-acetic acid (Compound IIIA)

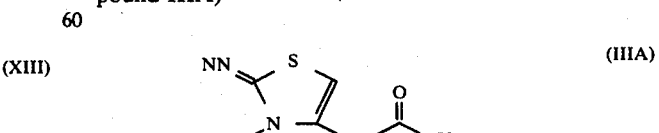

and ethyl 2-imino-3-aminothiazoline-4-acetate (Compound IIIB)

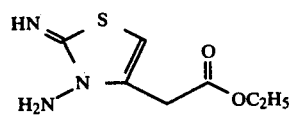

Compounds of formula (IV) include 2-amino-5-carbethoxymethylidene-4,5-dihydro-6H-1,3,4-thiadiazine (Compound IVA)

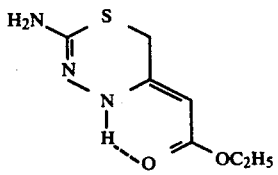

and 2-benzamido-5-carbethoxymethylidene-4,5-dihydro-6H-1,3,4-thiadiazine (Compound IVB)

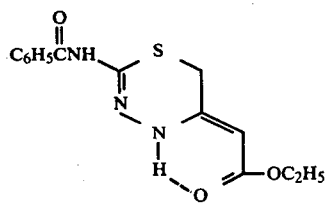

Compounds of formula (V) include ethyl 2-benzimido-3-benzoyl-2,3-dihydro-6H-1,3,4-thiadiazine-5-acetate (Compound VA)

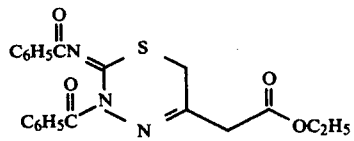

and 2-benzimido-3-benzoyl-5-ethyloxalyl-2,3-dihydro-6H-1,3,-4-thiadiazine oxime benzoate (Compound VB)

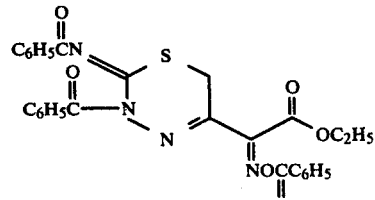

Compounds of formula (VI) include 2-amino-5-ethyloxalyl-6H-1,3,4-thiadiazine oxime (Compound VIA)

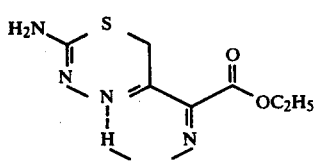

2-amino-5-ethyloxalyl-6H-1,3,4-thiadiazine oxime benzoate (Compound VIB)

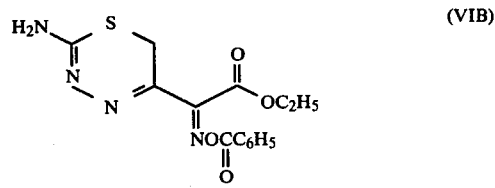

and 2-benzamido-5-ethyloxalyl-6H-1,3,4-thiadiazine oxime benzoata (Compound VIC)

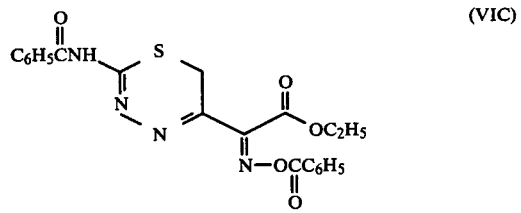

Compounds of formula VII include 4,5-dihydro-2-(2-benzoylhydrazino)-4-carbethoxymethylidenethiazoline-5-oxime (Compound VIIA)

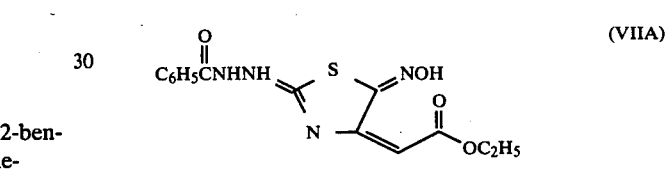

and 4,5-dihydro-2-(isopropylidinehydrazono)-4-carbethoxy-methylidinethiazoline-5-oxime (Compound VIIB)

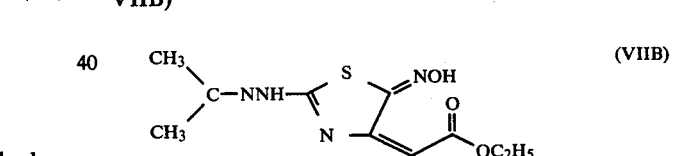

Certain of the compounds may be obtained directly by reacting thiosemicarbazide and ethyl 4-chloroacetoacetate under varying reaction conditions, and the balance are produced by dehydrating, neutralizing, nitrosating and benzoylating the direct reaction products. These compounds have demonstrated utility as herbicides.

DESCRIPTION OF THE DRAWING

The drawing illustrates reaction schemes for producing the compounds of this invention.

DETAILED DESCRIPTION OF THE PREFERRED EMBODIMENTS

It has been found that condensation of thiosemicarbazide, $NH_2NHCSNH_2$, with ethyl 4-chloroacetoacetate, $ClCH_2COCH_2COOC_2H_5$, yields thiadiazine, thiazole, or thiazoline condensation products, depending on the acidity and polarity of the solvent employed and on reaction temperature. Thus, ethyl 2-amino-6H-1,3,4-thiadiazine-5-acetate (Compound IA) hydrochloride may be obtained by conducting the reaction in a polar, highly protic solvent such as acetonitrile or concentrated hydrochloric acid at ambient conditions. The product may be obtained but in less desirable yield using chloroform or ether solvents.

In contrast, ethyl 2-hydrazinothiazole-4-acetate (Compound IIA), a red oil, is obtained from the reaction of thiosemicarbazide and 4-chloroacetoacetate in aqueous ethanolic potassium acetate. Compound IIA in the presence of acetone yielded ethyl-2-isopropylidenehydrazonothiazole-4-acetate (Compound IIB).

Alternatively, the hydrochloride of Compound IIB may be obtained by reacting thiosemicarbazide and 4-chloroacetoacetate in acetone solvent or by first reacting acetone and thiosemicarbazide to obtain acetonethiosemicarbazone which is thereafter reacted with 4-chloroacetoacetate in acetone solvent. The free base (Compound IIB) may be obtained by treatment of the corresponding hydrochloride with base such as aqueous sodium bicarbonate solution. In addition, the free base (Compound IIB) may be obtained by reacting ethyl 2-amino-6H-1,3,4-thiadiazine-5-acetate (Compound IA) with acidic acetone, the ring structure contracting to give Compound IIB. These reactions are illustrated in Reaction Scheme 1 of the drawing.

Ethyl 2-benzylidenehydrazonothiazole-4-acetate (Compound IID), the corresponding benzaldehydehydrazono derivative of Compound IIB, is obtained by reacting benzaldehydethiosemicarbazone with ethyl-4-chloroacetoacetate.

Neutralization of compound IA using aqueous sodium bicarbonate resulted in the migration of a double bond outside the thiadiazine ring and yielded 2-amino-5-carbethoxymethylidene-4,5-dihydro-6H-1,3,4-thiadiazine (Compound IVA).

Reaction of thiosemicarbazide and ethyl 4-chloroacetoacetate in warm concentrated hydrochloric acid yielded 2-imino-3-aminothiazoline-4-acetic acid (Compound IIIA), which is also obtained by heating the hydrochloride of Compound IA in hydrochloric acid. Refluxing Compound IIIA in ethanolic hydrochloric acid produces the hydrochloride of the corresponding acetate, Compound IIIB (ethyl 2-imino-3-aminothiazoline 4-acetate.)

Neutralization of the hydrochloride of Compound III-A with sodium carbonate resulted in double bond migration and produced 2-imino-3-amino-4-carbethoxymethylidine thiazolidine (Compound X). These reactions are also illustrated in Scheme 1.

The foregoing compounds may be derivatized by benzoylation and nitrosation. Using benzoyl chloride, 2-amino-5-carbethoxymethylidene-4,5-dihydro-6H-1,3,4-thiadiazine (Compound IVA) may be converted to a variety of benzoylated derivatives. Thus, using a stoichiometric amount of benzoyl chloride in acetonitrile-pyridine solvent, 2-benzamido-5-carbethoxymethylidene-4,5-dihydro-6H-1,3,4-thiadiazine (Compound IVB) may be obtained. However, refluxing of compound IVA and benzoyl chloride in benzene yielded the hydrochloride of 2-benzamido-6H-1,3,4-thiadiazine-5-acetate (Compound IB). Neutralization of the hydrochloride of Compound IB also produced compound IVB.

Heating of compound IVA with an excess of benzoyl chloride in a chloroform-sodium bicarbonate suspension yielded a dibenzoylated product, ethyl 2-benzimido-3-benzoyl-2,3-dihydro-6H-1,3,4-thiadiazine-5-acetate (Compound VA), a compound which could also be obtained by heating the hydrochloride of Compound IB under the same conditions.

Stirring Compound IVA and excess benzoyl chloride in hot pyridine-acetonitrile or ethanol-triethylamine solvent produced 2-benzamido-4-benzoyl-5-carbethoxymethylidene-4,5-dihydro-6H-1,3,4-thiadiazine (Compound VIII). Thus, the benzoylation of Compound IVA is highly solvent dependent, non-polar solvents favoring production of compound VA while more polar systems tend to produce Compound VIII. These reactions are illustrated in Scheme 2 of the drawing.

Compound X may be selectively benzoylated at the imino functionality to yield ethyl 2-benzimido-3-aminothiazoline-4-acetate (Compound XIII) by employing benzoyl chloride in ethanol-triethylamine solvent, as shown in Scheme 3.

Certain derivatives in accordance with this invention may be made by initially preparing substituted thiosemicarbazides and thereafter condensing the resulting material with ethyl 4-chloroacetoacetate. Such an approach is shown in Scheme 4 in which ethyl 2-(2-benzoylhydrazino)thiazole-4-acetate (Compound IIC) hydrochloride is obtained by refluxing 1-benzoyl-3-thiosemicarbazide, C₆H₅CONHNHCSNH₂, with ethyl 4-chloroacetoacetate in ethanol. Neutralization of the hydrochloride of compound IIC produces the free base (Compound IIC).

Compound IIC undergoes a dehydrative cyclization in phosphoryl chloride-xylene medium to yield ethyl 3-phenylthiazolo[2,3 c]-s-triazole-4-acetate (Compound XI). Ethyl-2-phenylthiazolo[3,2b]-s-triazole-4-acetate (Compound XII), the structural isomer of compound (XI), may be obtained either by the dehydrative cyclization of compound XIII in phosphorylchloride-xylene or by condensing ethyl 4-chloroacetoacetate with 3-phenyl-1,2,4 triazole-5-thiol (Compound XIV). Compound XIV is prepared from 1-benzoyl-3-thiosemicarbizide refluxed in sodium ethoxide ethanol.

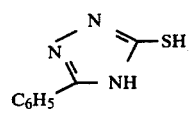

(XIV)

Preparation of nitrosated derivatives is illustrated in Schemes 5–7. Treatment of either the hydrochloride of compound IA or Compound IVA with nitrous acid produced 2-amino-5-ethyloxalyl-6H-1,3,4-thiadiazine oxime (Compound VIA).

Nitrosation of the hydrochloride of Compound IIC produced 4,5-dihydro-2(2-benzoylhydrazino)-4-carbethoxymethylidenethiazoline-5-oxime (Compound VIIA) as shown in Scheme 6.

Similarly, the hydrochloride of Compound IIB upon nitrosation yielded 4,5-dihydro-2-(isopropylidenehydrazono)-4-carbethoxymethylidenethiazoline-5-oxime (Compound VIIB) as shown in Scheme 7.

Benzoylation of Compound VIA with an excess of benzoyl chloride in acetonitrile pyridine produced a mixture of 2-amino-5-ethyloxalyl-6H-1,3,4-thiadiazine oxime benzoate (Compound VIB); 2-benzamido-5-ethyloxalyl-6H-1,3,4-thiadiazine oxime benzoate (Compound VIC); 2-benzamido-4-benzoyl-5-ethyloxalyl-4H-1,3,4-thiadiazine oxime benzoate (Compound IX); and 2-benzamido-3-benzoyl-5-ethyloxalyl-2,3-dihydro-6H-1,3,4-thiadiazine oxime benzoate (Compound VB).

This mixture may be separated by conventional techniques such as silica gel chromotography, or the individual compounds VIB, VIC, IX and VB may be selectively obtained as follows.

The monohydrate hydrochloride of compound VIB separated after stirring Compound VIA and benzoyl chloride at room temperature in acetonitrile. The resulting salt may be neutralized with sodium bicarbonate to produce the free base, Compound VIB. Solution of Compound VIB in acetonitrile-pyridrine at 0° C. with benzoyl chloride slowly added produced a white pyridinium complex which, upon recrystallization from methanol-chloroform-petroleum ether solvent, yielded compound VIC. Refluxing compound VIC with benzoyl chloride in acetonitrile-pyridine resulted in the preparation of the tribenzoylated aducts, Compounds VB and IX, which are separated by solubility.

These reactions are shown in Scheme 5.

As noted in a number of cases, especially where free bases are involved, the compounds may conveniently be isolated as stable acid addition salts such as hydrochlorides and the like.

The physical properties and other identifying characteristics of the novel compounds of this invention are shown in the following examples which provide detailed preparatory schemes.

Melting points are taken on a Mel-temp melting point apparatus and are uncorrected. Infrared spectra were determined on Perkin-Elmer models 137-B and 467 infrared spectrometers using potassium bromide pellets unless stated otherwise. With deuteriochloroform or hexadeuteriodimethylsufoxide as solvents, nuclear magnetic resonance spectra were determined on a Varian Associates Model EM-360 spectrometer; the high resolution experiment was performed on a Varian HR 220 MHz High Resolution spectrometer. The electronic spectra were obtained in ethanol on a Bausch and Lomb 505 spectrometer, with molar absorptions recorded to only two significant figures. At 70 eV a Varian Mat CH-7 spectrometer recorded the mass spectra. Elemental analysis were performed at Midwest Micro Labs, Inc., Indianapolis, Indiana.

In thin layer chromatography separations, Kodak silica gel sheets were utilized. Chromatographic columns were constructed of silica gel pellets.

EXAMPLE 1

Ethyl 2-Amino-6H-1,3,4-thiadiazine-5-acetate (Compound IA) Hydrochloride.

To a stirred suspension of thiosemicarbazide (14.0 g., 0.15 mole) in acetonitrile (450 ml.), 26.5 g. (0.15 mole) of ethyl 4-chloroacetoacetate was added. Heating caused solution, and after 6 hours at 60°, the white hydrochloride of Compound IA (24 g., 67%) precipitated upon cooling. The product was washed thoroughly with chloroform after filtration and recrystallized from ethanol, m.p. 147°-148°; ir (potassium bromide): 3220-2640 (N—H+), 1730 (C=O), 1600, 1560 (C=N) cm$^{-1}$; uv λmax (ethanol) nm (log ε): 220 (14.3), 258 (9.5), 344 (7.1); pmr (deuteriodimethylsulfoxide, deuteriochloroform): δ1.22 (t, 3H, —CH$_3$), 3.73 (s, 2H, S—CH$_2$), 3.83(s, 2H, CH$_2$CO), 4.20 (q,2H, OCH$_2$).

Anal. Calcd. for C$_7$H$_{12}$ClN$_3$O$_2$S: C, 35.36; H, 5.10; Cl, 14.92; N, 17.68; S, 13.47; m.w.—HCl,201. Found: C,35.48, H, 5.15; Cl, 15.17; N, 17.91; S, 13.77; M+, 201.

With chloroform, ethyl ether, or tetrahydrofuran as solvents, the above condensation was carried out at room temperature. Since these reaction mixtures were heterogeneous throughout, a large excess of solvent was needed. The product was usually colored yellow and had to be recrystallized several times from ethanol. Refluxing or stirring at room temperature in ethanol produced a complex mixture out of which impure Compound IA hydrochloride crystallized. The reaction also occurred in concentrated hydrochloric acid at room temperature (as a suspension). The percent yields and melting points for the crude product from various solvent systems are given in Table 1. As noted, the compounds of this invention may be obtained in free compound form or in the form of stable acid addition salts such as hydrochlorides.

TABLE 1

Condensation of Ethyl 4-Chloroacetoacetate with Thiosemicarbazide in Various Solvents

| Solvent | IA HCl, % Yield | Appearance | M.p. |
|---|---|---|---|
| Ethanol, reflux | 34 | dark yellow | 137–143° |
| Ethanol, room temperature | 37 | yellow | 138–143° |
| Chloroform, room temp. | 40 | yellow | 138–143° |
| Tetrahydrofuran, room temp. | 50 | yellow tint | 140–144° |
| Ethyl ether, room temp. | 55 | yellow tint | 142–145° |
| Concentrated hydrochloric acid, room temperature | 60 | off white | 143–146° |
| Acetonitrile, warming | 67 | colorless | 146–148° |

These reactions were heterogeneous and the % yield was based on the amount of product obtained after the first crystallization from ethanol.

EXAMPLE 2

Ethyl 2-Benzamido-6H-1,3,4-thiadiazine-5-acetate (Compound IB) Hydrochloride.

A mixture of Compound IVA (Example 12) (3.0 g., 15.0 mmoles) and benzoyl chloride (5.0 g., 35.7 mmoles) in 100 ml. of benzene was refluxed for 14 hours. After cooling, the organic solution was washed with water (to remove traces of Compound IA hydrochloride), dried over calcium chloride, filtered, and concentrated under reduced pressure. Upon addition of a small amount of petroleum ether to the final reaction solution, white (Compound IB) hydrochloride slowly separated from solution (3.0 g., 59%). Thin layer chromatography revealed a number of compounds present in the filtrate. The hydrochloride of Compound IB was fairly soluble in chloroform but not so in water; m.p. 156°-158° (ethanol); ir (potassium bromide): 3200-2300 (N—H+), 1725, 1675 (C=O), 1590-1490 (C=N) cm$^{-1}$; pmr (deuteriochloroform): δ1.40 (t, 3H, CH$_3$), 3.70 (s, 2H, SCH$_2$), 3.85 (s, 2H, CH$_2$CO), 7.55-7.85 (m, 3H, ArH), 8.30-8.65 (m,2H,ArH).

Anal. Calcd. for C$_{14}$H$_{16}$ClN$_3$O$_3$S: C, 49.18; H, 4.73; Cl: 10.38; N, 12.29; S, 9.37. Found: C, 48.92; H, 4.75; Cl, 10.57; N, 12.39; S, 9.18.

EXAMPLE 3

Ethyl 2-Hydrazinothiazole-4-acetate (Compound IIA).

Potassium acetate (1.3 g., 12.5 mmoles) was dissolved in 40 ml. of an aqueous ethanol mixture (1:1). With stirring, thiosemicarbazide (1.1 g., 12.5 mmoles) and ethyl 4-chloroacetoacetate (2.0 g., 12.5 mmoles) were introduced. After 3 hours of stirring at room temperature a red oil settled out. The reaction mixture was diluted with water and extracted several times with methylene chloride (total 100 ml.). Combined extracts were dried (calcium chloride), filtered, and concentrated under reduced pressure to approximately 2.0 g. of oily residue. Thin layer chromatography (chloroform) revealed the presence of two compounds. This oil was then chromatographed on a silica gel column using methylene chloride as the eluent. Compound IVA (see Example 12) was in the first few fractions while the latter fractions contained a single component (0.6 g.) characterized as Compound IIA by pmr. Although Compound IIA was chromatographically pure, it would not crystallize; ir (mull): 3450-3200 (N—H), 1725 (C=O), 1620, 1580 (C=N) cm$^{-1}$: pmr (deuteriochloroform): $\delta$1.20 (t, 3H, CH$_3$), 3.55 (s, 2H, CH$_2$CO), 4.15 (q, 2H, OCH$_2$), 5.80-6.20 (s-broad, 3H, NH), 6.30 (s, 1H, vinyl); ms: (m/e)201(M+).

EXAMPLE 4

Ethyl 2-Isopropylidenehydrazonothiazole-4-acetate (Compound IIB) Hydrochloride.

A suspension of thiosemicarbazide (4.5 g., 50.0 mmoles) and 1 (8.2 g., 50.0 mmoles) in 175 ml. of acetone was magnetically stirred at room temperature for 18 hours. The insoluble white hydrochloride of Compound IIB was separated (11.9 g., 86%) from the milky white mixture and dissolved in ethanol by heating. Upon cooling, colorless Compound IIB hydrochloride crystallized, m.p. 171-173 deg.; ir (potassium bromide): 3120-2640 (N—H+), 1725 (C=O), 1590 (C=N) cm$^{-1}$; nmr (deuteriodimethylsulfoxide, deuteriochloroform): $\delta$1.30 (t, 3H, CH$_3$), 2.10 (d,6H,(CH$_3$)$_2$ C=N,J=3 Hz), 3.80 (s, 2H, CH$_2$CO), 4.15 (q, 2H, OCH$_2$), 6.88(s, 1H, vinyl).

Anal. Calcd. for C$_{10}$H$_{16}$ClN$_3$O$_2$S: C, 43.23; H, 5182; Cl, 12.77; N, 15.13; m.w.—HCl, 241. Found: C, 42.95; H, 5.88; Cl, 13.29; N, 15.30; S, 11.94; M+, 241.

Analogous results were obtained when reacting acetonethiosemicarbazone with ethyl 4-chloroacetoacetate in acetone. Stirring at room temperature 2.9 g., (25.0 mmoles) of acetonethiosemicarbazone and 4.1 g., (25.0 mmoles) of ethyl 4-chloroacetoacetate in acetone (100 ml.) for 15 hours yielded 5 g., (72%) of Compound IIB hydrochloride.

EXAMPLE 5

Ethyl 2-Isopropylidenehydrazonothiazole-4-acetate (Compound IIB)

The hydrochloride of Compound IIB (4.0 g., 14.4 mmoles) was dissolved in 125 ml. of water and neutralized with 5% sodium bicarbonate solution at room temperature. After complete neutralization, white product gradually formed (2.7 g., 78%). When first isolated after filtration and washed with water, the precipitate was off-white but upon setting in air turned yellow. Crystallization (ethanol, water) yielded the yellow free base, Compound IIB. Both the white and yellow products gave identical melting points and matching spectral properties. Gas chromatography produced a single peak for the yellow free base Compound IIB but showed a slight impurity for the initial white product, m.p. 68-69 degrees; ir (potassium bromide): 3330 (N—H), 1725 (C=O), 1570 (C=N) cm$^{-1}$; pmr (deuteriochloroform); $\delta$1.35 (t, 3H, CH$_3$), 1.94 (d, 6H, J=12 Hz, N=C(CH$_3$)$_2$), 3.82 (s, 2H, CH$_2$CO), 4.22 (q. 2H, OCH$_2$), 6.50 (s, 1H, vinyl).

Anal. Calcd. for C$_{10}$H$_{15}$N$_3$O$_2$S: C, 49.76; H, 6.28; N, 17.42; S, 13.27; m.w., 241. Found: C, 49.55; H, 6.17; N, 17.23; S, 13.14; M+, 241.

The hydrochloride of Compound IA (2.0 g., 8.4 mmoles) was dissolved in 80 ml. of water and 10 ml of acetone and heated on a steam bath for 10 minutes. The free base of Compound IIB (1 g., 49%) was isolated after neutralized at 0° with 10% sodium bicarbonate. Simple addition of acetone also converted Compound IIA to Compound IIB.

EXAMPLE 6

Reaction of Ethyl 4-chloroacetoacetate and Acetonethiosemicarbazone in Ethanol.

Ethyl 4-chloroacetoacetate (4.0 g., 25.0 mmoles) was slowly added to 2.9 g. (25.0 mmoles) of acetonethiosemicarbazone dissolved in 100 ml. of ethanol. The solution was warmed with constant stirring until the original green color turned yellow (approximately 1 hour). Only a small amount (0.6 g., 9%) of the white Compound IIB hydrochloride precipitated after cooling. Refluxing the filtrate for 2 hours produced a deep-red solution, and upon cooling, impure crystals of Compound IA hydrochloride separated (1.1 g., 19%), identified by m.p. and ir.

EXAMPLE 7

Ethyl 2-(2-Benzoylhydrazino)-thiazole-4-acetate (Compound IIC) Hydrochloride.

Using the procedure disclosed in E. Hoggarth, J. Chem. soc., 1167(1949), 1-benzoyl-3-thiosemicarbazide was prepared by suspending powered thiosemicarbazide (3.0 g., 33.0 mmoles) in dry pyridine (33 ml.) and cooling to 0°. Benzoyl chloride (5.0 g., 35.7 mmoles) was added dropwise at 0° for 1.5 hours. After 14 hours of stirring at room temperature, 170 ml. of water were added and the pyridine removed under reduced pressure. The oily precipitate was dissolved in hot water, filtered, and allowed to cool to give 4.0 g (62%) of colorless leaflets melting at 196°-198° after several crystallizations.

A mixture of 1 benzoyl-3-thiosemicarbazide (3.0 g., 15.0 mmoles) and ethyl 4-chloroacetoacetate (2.48 g., 15 mmoles) was refluxed 6 hours in 100 ml. of absolute ethanol to form a clear yellow solution. By slowly adding ethyl ether to the chilled concentrated solution, 4.0 g., (78%) of white Compound IIC hydrochloride settled out. The compound was recrystallized, (ethanol, ether). Compound IIC hydrochloride melted at 172°-196°; ir (potassium bromide): 3330-2500 (N—H+), 1725 O (C=O), 1675, 1630 (C=O, C=N) cm$^{-1}$; pmr (deuteriodimethylsulfoxide, deuteriochloroform): $\delta$ 1.25 (t, 3H, CH$_3$), 3.72 (s, 2H, CH$_2$CO), 4.18 (q, 2H, OCH$_2$), 6.90 (s, 1H, vinyl), 7.50-7.80 (m, 3H, ArH), 8.05-8.33 (m, 2H, ArH).

Anal. Calcd. for C$_{14}$H$_{15}$O$_3$N$_3$SC: C, 49.32; H, 4.45; N, 12.33; S, 9.40; m.w., —HCl, 305. Found: C, 49.53; H, 459; N, 12.38; S, 9.69; M+, 305.

EXAMPLE 8

Ethyl 2-(2-Benzoylhydrazino)-thiazole-4-acetate (Compound IIC)

Neutralization at 0° of 4.0 g. (11 7 mmoles) of Compund II-C hydrochloride in aqueous-methanol solution (100 ml., 1:4) with 10% sodium bicarbonate, precipitated 3.0 g. (84%) of the free base Compound IIC. More water (100 ml.) was added, the product collected and crystallized from propanol to give colorless crystals melting at 151°-153°; ir (potassium bromide): 3330 (N—H), 1725, 1688 (C=O), 1600 (C=N) cm$^{-1}$; uv, $\lambda$max (ethanol): nm(log $\epsilon$) 240 (26.9), 263 (13.8): pmr (deuteriochloroform): δ1.24 (t, 3H, CH$_3$), 3.65 (s, 2H, CH$_2$CO), 4.18 (q, 2H, OCH$_2$), 6.52 (s, 1H, vinyl), 7.35–8.25 (m, 5H, ArH).

Anal. Calcd. for C$_{14}$H$_{15}$N$_3$O$_3$S: C, 55.05; H, 4.96; N, 13.77; S, 10.49; m.w., 305. Found: C, 54.96; H, 5.00; N, 13.70; S, 10.38; M+, 305.

EXAMPLE 9

Ethyl 2-Benzylidenehydrazonothiasole-4-acetate (IID)

To 3.0 g. (18.1 mmoles) of benzaldehydethiosemicarbazone and 1.82 g. of triethylamine in 125 ml. of ethanol, 4-chloroacetoacetate (2.96 g., 18.1 mmoles) was added. Immediately the reaction turned black; this dark solution was heated with constant stirring for 8 hours. Yellow IID separated (4.4 g., 86%) after water was added dropwise to the chilled reaction solution, m.p. 134°–136° (ethanol, water); ir (potassium bromide): 3440 (N—H), 1725 (C=O), 1570 (C=N) cm$^{-1}$; uv λmax (ethanol)nm(log ε): 248 (14.2), 344 (18.4); pmr (deuteriochloroform): δ1.25 (t, 3H, CH$_3$), 3.72 (s, 2H, CH$_2$CO), 4.20, (q, 2H, OCH$_2$), 6.50 (s, 1H, vinyl), 7.20–7.75 (m, 5H, ArH), 7.85 (s, 1H, benzylidene-H), 8.35 (s, 1H, N—H).

Anal. Calcd. for C$_{14}$H$_{15}$N$_3$O$_2$S: C, 58.10; H, 5.24; N, 14.53; S, 11.07; m.w., 289. Found: C, 57.88; H, 5.23; N, 14.57; S, 11.03; M+, 289.

EXAMPLE 10

2-Imino-3-aminothiazoline-4-acetic Acid (Compound IIIA Hydrochloride.

Addition of the Compound IA hydrochloride (23.0 g., 97.0 mmoles) to concentrated hydrochloric acid (70 ml.), followed by heating (20 minutes) gave a clear solution. Eventually, white hydrochloride (Compound IIIA) (16.0 g., 79%) crystallized. Collected on a glass filter and washed several times with chloroform, the product (Compound IIIA hydrochloride) was crystallized from a methanol mixture. The dried thiazoline (Compound IIIA) hydrochloride melted at 220°–223° (dec.); ir (potassium bromide): 3300–2630 (N—H+), 1720–1690 (C=O), 1625–580 cm$^{-1}$; uv, λmax (ethanol): nm (log ε) 262 (3.50); pmr (deuteriodimethylsulfoxide, deuteriochloroform): δ3.83 (s, 2H, CH$_2$CO), 6.50 (s-broad, 3H, N—H), 6.80 (s, 1H, vinyl), 9.70 (s-broad, 1H, OH).

Anal. Calcd. for C$_5$H$_8$ClN$_3$O$_2$S: C, 28.64; H, 3.86; Cl, 16.92; N, 20.04; S, 15.27. Found: C, 28.51; H, 385; Cl, 17.12; N, 20.26; S, 15.08.

EXAMPLE 11

Ethyl 2-Imino-3-aminothiazoline-4-acetate (Compound IIIB) Hydrochloride.

Suspended in 250 ml. of ethanol, 7.0 g. (30.0 mmoles) of the acid (Compound IIIA) hydrochloride and 4 ml. of 6N hydrochloric acid were refluxed for 35 hours; a solution gradually formed. The ester (Compound IIIB) hydrochloride was precipitated (5.0 g., 67%) by slowly adding ethyl ether into the concentrated solution. At shorter reaction times, a mixture of the acid (Compound IIIA) hydrochloride and ester (Compound IIIB) hydrochloride was obtained.

Compound IIIB hydrochloride melted at 154°–155° (ethanol ethyl ether); ir (potassium bromide): 3320–2700 (N—N+), 1725–1690 (C=O), 1625–1580 (C=N) cm$^{-1}$; uv λmax (ethanol): nm (log ε) 263 (3.70), pmr (deuteriodimethylsulfoxide, deuteriochoroform): δ1.15 (t, 3H, CH$_3$), 3.83 (s, 2H, CH$_2$CO), 4.20 (q, 2H, CH$_2$O), 6.80 (s, 1H, vinyl), 9.60 (s-broad, 1H, NH)

Anal. Calcd. for C$_7$H$_{12}$ClN$_3$O$_2$S: C, 35.36; H, 5.10; Cl, 14.92; N, 17.68; S, 13.47. Found: C, 35.64; H, 5.17; Cl, 14.85; N, 17.87; S, 13.42.

EXAMPLE 12

2-Amino-5-carbethoxymethylidene-4,5-dihydro-6H-1,3,4-thiadiazine (Compound IVA).

A 4.0 g. sample of Compound IA hydrochloride (17.0 mmoles) was dissolved in 60 ml. of distilled water and chilled to 0°. Sodium bicarbonate solution (10%) was slowly titrated into the stirred aqueous solution until neutrality was reached, detected with pH paper. A white precipitate eventually settled out. After filtering, washing with water, and drying under vacuum at 60°, the yellow free base Compound IVA was isolated (2.4 g., 70%). The original white precipitate isomerized to a mixture of Compound IA and Compound IVA in solution, as monitored by pmr. Crystallization of Compound IVA from benzene generated yellow diamond shaped crystals, m.p. 123°–125°; ir (potassium bromide); 3450, 3350 (N—H), 1670–1560 (C=O, C=N) cm$^{-1}$; uv, λmax (ethanol): nm (log ε) 248 (5.7), 345 (10.1); pmr (deuteriochloroform): δ1.25 (t, 3H, CH$_3$), 3.45 (s, 2H, SCH$_2$), 4.15 (q, 2H, OCH$_2$), 4.45 (s, 1H, vinyl), 4.70 (s, 2H, NH$_2$), 10.50 (s, 1H, hydrogen bonded N—H).

Anal. Calcd. for C$_7$H$_{11}$N$_3$O$_2$S: C, 41.77; H, 5.52; N, 20.88; S, 15.91; m.w., 201. Found: C, 42.12; H, 5.62; N, 20.60; S, 15.62; M+, 201.

If an aqueous solution of Compound IA hydrochloride was neutralized with 10% sodium bicarbonate before addition of acetone, only the formation of Compound IVA free base resulted.

A solution of Compound IVA (1.0 g., 5.0 mmoles) in 35 ml. of chloroform was acidified with 6 drops of concentrated hydrochloric acid and stirred for 2 hours at room temperature. Gradually a solid separated (1.0 g., 84%). When filtered and dried it melted at 146°–148° identical to Compound IA hydrochloride in melting point and ir spectrum.

EXAMPLE 13

2-Benzamido-5-carbethoxymethylidene-4,5-dihydro-6H-1,3,4-thiadiazine (Compound IVB).

To a solution of the Compound IVA (4.0 g., 20.0 mmoles) dissolved in 100 ml. of acetonitrile and 2.5 ml. of pyridine, benzoyl chloride (2.8 g., 20.0 mmoles) in acetonitrile (80 ml.) was added dropwise over a period of 1.5 hours at 0°. The yellow solution was stirred for 8 hours at room temperature then heated 2 hours. A small amount of Compound IA hydrochloride was filtered after sitting 2 hours at room temperature. Concentrated, the filtrate was transferred to a separatory funnel, and ether (250 ml.) and water were added. The aqueous layer was separated, and the organic layer washed several more times with water to remove traces of pyridine. When the ether solution was dried (calcium chloride) and concentrated; 2.4 g. (40%) of Compound IVB crystallized, m.p. 149°–151° after recrystallization from ethanol; ir (potassium bromide): 3220 (N—H, 1625–1550 (C=O, C=N), cm$^{-1}$; uv, λmax (ethanol): nm (log ε) 255 (6.6), 360 (11.2); pmr (deuteriochloroform): δ 1.13 (t, 3H, CH$_3$), 3.50 (S, 2H, SCH$_2$), 3.72 (q, 2H, CH$_2$CO), 4.45 (s, 1H, vinyl), 7.35–7.75 (m, 3H, ArH), 7.95–8.20 (m, 2H, ArH), 10.23 (s, 1H, hydrogen bonded, N—H), 11.50 (s, 1H, amide N—H).

Anal. Calcd. for $C_{14}H_{15}N_3O_3S$: C, 55.05; H, 4.96; N, 13.77; S, 10.49. Found: C, 55.10; H, 4.91; N, 13.52; S, 10.27.

Compound IB hydrochloride (1.0 g., 3.0 mmoles) in a 300 ml. round bottom flask was dissolved in 50 ml of an ethanol-water mixture (4:1) and chilled in an ice bath. Sodium bicarbonate (10%) was added while the reaction mixture was being stirred. After a white product began to form additional water was introduced. Filtration and vacuum drying yielded yellow crystals (0.65 g., 71%) with an identical melting point and ir spectrum to Compound IVB free base.

EXAMPLE 14

Ethyl 2-Benzimido-3-benzoyl-2,3-dihydro-6H-1,3,4-thiadiazine-5-acetate VA.

Compound IVA (1.0 g., 5.0 mmoles) was dissolved in 40 ml. of chloroform and an excess of sodium bicarbonate (1.5 g., 18.0 mmoles) was introduced. An excess of benzoyl chloride (3.5 g., 25.0 mmoles) was then added, the suspension refluxed for 8 hours, and then allowed to stand for several hours at room temperature. The insoluble salts were filtered and the filtrate concentrated under reduced pressure. With slow addition of a petroleum ether-isopropanol mixture (1:1), white Compound VA immediately precipitated (1.6 g., 78%). Colorless leaflets of Compound VA melted at 146°–148° (2-propanol); ir (potassium bromide): 1715–1720 (C=O), 1650–1580 (C=N) cm$^{-1}$; uv λmax (ethanol): nm (log ε) 255 (19.2), 265 (20.0); pmr (deuteriochloroform): δ1.33 (t, 3H, CH$_3$), 3.65 (s, 2H, SCH$_2$), 3.75 (s, 2H, CH$_2$CO), 4.25 (q, 2H, OCH$_2$), 7.00–8.20 (m, 10H, ArH).

Anal. Calcd. for $C_{21}H_{19}N_3O_4S$: C, 61.59; H, 4.69; N, 10.26; S, 7.82; m.w., 409. Found: C, 61.31; H, 4.70; N, 10.26; S, 7.60; M+, 409.

EXAMPLE 15

2-Amino-5-ethyloxalyl-6H-1,3,4-thiadiazine Oxime (Compound VIA)

Sodium nitrite (6.9 g., 0.10 mole) in 70 ml. of water was added dropwise to a reaction flash containing 24.0 g. (0.10 mole) of Compound IA hydrochloride dissolved in 150ml. of water, chilled in an ice bath. Stirring gradually produced a light yellow solution at which time off-white product began to precipitate. This product was constantly filtered off throughout the reaction at varying intervals of time. If the precipitate was allowed to set in the reaction medium, it turned brown. The filtered portions of the crude material were combined to give 18 g. of product. Recrystallized from aqueous ethanol, colorless crystals which analyzed correctly for $C_7H_{10}N_4O_3S$ were obtained; but thin layer chromatography (methanol-2 N hydrochloric acid, 8:1) demonstrated the presence of two substances. Successive crystallizations from aqueous methanol did not remove the impurity, nor could it be separated by column chromatography. When the material (1.10 g.) was refluxed in acetone for 20 hours (never going completely into solution), 0.7 g. of pure white product, characterized as Compound VIA was collected.

The original recrystallized product mixture exhibited carbonyl stretchings at 1725 and 1690 cm$^{-1}$ in the ir. Compound VIA insoluble in acetone, absorbed solely at 1725 cm$^{-1}$, while the impure yellow material isolated by concentrating the bright acetone filtrate showed an enhanced absorption at 1690 cm$^{-1}$, along with the 1725 cm$^{-1}$ band.

Compound VIA melted at 188°–191° (methanol); ir (potassium bromide): 3450, 3330 (N—H), 2870–2230 (=N—OH), 1725 (C=O), 1610 (C=N) cm$^{-1}$; uv, λmax (ethanol); nm (log ε) 268 (9.9), 312 (7.4), 337 (6.2); pmr (deuteriodimethylsufoxide, deuteriochloroform): δ1.30 (t, 3H, CH$_3$), 3.50 (s, 2H, SCH$_2$), 4.40 (q, 2H, OCH$_2$).

Anal. Calcd. for $C_7H_{10}O_3N_4S$: C, 36.51; H, 4.39; N, 24.34; S, 13.91; .w., 230. Found: C, 36.74; H, 4.63; N, 24.17; S, 13.62; M+, 230.

Nitrosating the yellow free base (Compound IVA) with an equivalent of hydrochloric acid in aqueous solution under the same reaction conditions yielded the same product mixture.

EXAMPLE 16

2-Amino-5-ethyloxalyl-6H-1,3,4-thiadiazine Oxime Benzoate (Compound VIB) Hydrate Hydrochloride.

Without further purification, crude oxime (Compound VIA) throughly dried, (16.0 g., 70.0 mmoles) was suspended in 300 ml. of acetonitrile. Benzoyl chloride (10.0 g., 70.0 mmoles) diluted with acetonitrile (50 ml.) was added at room temperature. After stirring the clear yellow solution for 1 hour at room temperature, white product began to precipitate. The reaction mixture was allowed to sit for 12 hours, then filtered to give 20 g. (74%) of Compound VIB hydrochloride which melted at 182°–185° following crystallization from chloroform-methanol. A hydrochloride hydrate was indicated by the elemental analysis and spectra: ir (potassium bromide): 3330–2500 (N—H+), 1735 (C=O), 1625–1610 (C=N) cm$^{-1}$; pmr (deuteriodimethylsufoxide, deuteriochloroform): 1.32 (t, 3H, CH$_3$), 4.34 (s, 2H, S—CH), 4.53 (q, 2H, OCH$_2$), 7.40–8.15 (m, 5H, ArH).

Anal. Calcd. for $C_{14}H_{17}ClN_4O_5S$: C, 43.23; H, 4.42; N, 14.41; S, 8.23; m.w., —HCl, 334. Found: C, 43.36; H, 4.49; N, 14.34; S, 7.82; M+, 334.

EXAMPLE 17

2-Amino-5-ethyloxalyl-6H-1,3,4-thiadiazine Oxime Benzoate (Compound VIB)).

In an aqueous ethanol solution (200 ml., 2:1) the hydrochloride hydrate of Compound VIB (10 g., 26.0 mmoles) was neutralized dropwise at room temperature with 10% sodium bicarbonate. Almost instantaneously a greenish-yellow free base precipitated from solution. Complete neutralization, filtering, and drying resulted in 8 g. (92%) of Compound VIB which decomposed at 156°–159° after recrystallizing from 2-propanol; ir (potassium bromide): 3450–3100 (N—H), 1735 (C=O), 1625–1610 (C=N) cm$^{-1}$; uv, λmax (ethanol): nm (log ε) 251 (10.0), 280 (10.0) 372 (6.3); pmr (deuteriochloroform):

1.39 (t, 3H, CH$_3$), 3.73 (s, 2H, SCH$_2$), 4.45 (q, 2H, OCH$_2$), 5.10 (s-broad, 2H, NH$_2$), 7.43–7.75 (m, 3H, ArH), 7.95–8.20 (m, 2H, ArH).

Anal. Calcd. for $C_{14}H_{14}N_4O_4S$: C, 50.28; H, 4.23; N, 16.76; S, 9.58; m.w., 334. Found: C, 49.98; H, 3.97; N, 16.74; S, 9.54; M+, 334.

EXAMPLE 18

2-Benzamido-5-ethyloxalyl-6H-1,3,4-thiadiazine Oxime Benzoate (Compound VIC).

Benzoyl chloride (1.26 g., 9.0 mmoles) in acetonitrile (40 ml.) was dropped into a chilled suspension of the monobenzoylated oxime Compound VIB (3.0 g., 9.0 mmoles), in acetonitrile (100 ml.), containing 2 ml. of pyridine over a period of 1.5 hours with stirring. Addition of all the acid chloride caused formation of a clear yellow solution. A white precipitate settled after continual stirring for 2 hours. After standing for 10 hours at room temperature, 3.6 g. of a pyridinium complex was filtered, which melted at 154°–157° and was insoluble in chloroform. When recrystallized from a methanol-chloroform-petroleum ether system, the dibenzoylated free base (Compound VIC) was isolated (2.9 g., 73%). Readily soluble in chloroform, Compound VIC melted at 195°–197°; ir (potassium bromide): 3250 (N—H), 1730-1720 (C=O), 1620-1560 (C=O, C=N) cm$^{-1}$; uv, λmax (ethanol): nm (log ε) 258 (22.0), 351 (21.0); pmr (deuteriochloroform): δ1.45 (t, 3H, CH$_3$), 3.90 (s, 2H, SCH$_2$), 4.53 (q, 2H, OCH$_2$), 7.35-7.85 (m, 6H, ArH), 8.00-8.50 (m, 5H, ArH, N—H).

Anal. Calcd. for C$_{21}$H$_{18}$N$_4$O$_5$S: C, 57.51: H, 4.15; N, 12.78; S, 7.30; m.w., 438. Found: C, 57.14; H, 4.20; N, 12.49; S, 7.20; M+, 438.

EXAMPLE 19

4,5-dihydro-2(2-benzoylhydrazino)-4-carbethoxymethylidene thiazoline-5-oxime (Compound VIIA).

Slow addition of aqueous (20 ml.) sodium nitrite (0.8 g., 12.0 mmoles) to a stirred solution (150 ml., 1:1 methanol-water mixture) of Compound IIC hydrochloride (4.0 g., 12.0 mmoles) was carried out in an ice bath. A few drops of 6 N hydrochloric acid was added during the addition. The mixture was then stirred for 10 hours at room temperature, while precipitation of impure yellow Compound VIIA (3.0 g., 75%) gradually occurred. After recrystallizing several times from ethanol, off-white crystals of Compound VIIA were obtained, which melted at 194°–198°; ir (potassium bromide): 3220-2700 (N—H, =N—OH), 1680 (C=O), 1640-1580 (C=O, C=N) cm$^{-1}$; uv, λmax (ethanol) nm (log ε): 237 (14.7), 327 (17.2); pmr (hexadeuteriodimethylsulfoxide, deuteriochloroform); δ1.25 (t, 3H, CH$_3$), 4.22 (q, 2H, OCH$_2$), 5.70 (s, 1H, vinyl), 7.20-8.18 (m, 5H, ArH), 12.85 (s-broad, 2H, N—H).

Anal. Calcd. for C$_{14}$H$_{14}$N$_4$O$_4$S: C, 50.28; H, 4.23; N, 16.76; S, 9.58; m.w., 334. Found: C, 50.21; H, 4.24; N, 16.55; S, 9.37; M+, 334.

EXAMPLE 20

4,5-dihydro-2-(isopropylidinehydrazono)-4-carbethoxymethylidene thiazoline-5-oxime (Compound VIIB)

A solution of sodium nitrite (0.5 g., 7.2 mmoles) in 20 ml. of water was slowly added to a magnetically stirred aqueous solution (40 ml.) of Compound II-B hydrochloride (2.0 g., 7.2 mmoles) at 0°. The mixture was allowed to reach room temperature with stirring for 7 hours. By that time, 1.8 g. (90%) of yellow Compound VIIB had settled out of solution and was collected. This compound was quite hygroscopic, vacuum drying caused a 10% weight loss after oven drying for several days. Crystallization was achieved in benzene-chloroform, m.p. 175°–177°; ir (potassium bromide): 3330 (N—H), 3200-3780 (=N—H), 1675-1575 (C=O, C=N); uv, λmax (ethanol): nm (log ε) 257 (12.5), 346 (19.4); pmr (deuteriochloroform): δ1.25 (t, 3H, CH$_3$), 2.05 (s, 6H, (CH$_3$)$_2$C), 4.24 (q, 2H, OCH$_2$), 5.83 (s, 1H, vinyl), 10.61 (s-broad, 2H, N—H).

Anal. Calcd. for C$_{10}$H$_{14}$N$_4$O$_3$S: C, 44.42; H, 5.23; N, 20.73; S, 11.85; m.w., 270. Found: C, 44.61; H, 5.22; N, 20.67; S, 11.67; M+, 270.

EXAMPLE 21

2-Benzamido-4-benzoyl-5-carbethoxymethylidene-4,5-dihydro-6H-1,3,4-thiadiazine (Compound VIII).

A solution of 10 g. (0.071 mole) of benzoyl chloride in 70 ml. of acetonitrile was added dropwise to an ice cold solution of 6 g. (30 mmoles) of Compound IVA and 8 ml. of pyridine in 125 ml. of acetonitrile with stirring. The clear orange solution was refluxed for 12 hours, concentrated, taken up in ether (250 ml.) and washed several times with water. The ether was then dried (calcium chloride) and evaporated, leaving an oily brown residue, which when triturated in hot ethanol (150 ml.), solidified to a yellow solid (3.0 g.). Approximately 1.5 g. of impure Compound IVB was isolated from the ethanol filtrate on concentration. Colorless crystals of Compound VIII (1.9 g., 16%) m.p. 187°–189°, were obtained after recrystallizing the yellow solid from a methanolchloroform-petrolium ether mixture: ir (potassium bromide): 3220(N—H), 1690, 1670, 1640, 1580, (C=O, C=N) cm$^{-1}$; uv, λmax (ethanol): nm (log ε) 258 (20.1), 295 (20.1); pmr (hexadeuteriodimethylsulfoxide, deuteriochloroform): δ1.30 (t, 3H, CH$_3$), 3.80 (s, 2H, SCH$_2$), 4.13 (q, 2H, OCH$_2$), 6.00 (s, 1H, vinyl), 7.35-8.25 (m, 10H, ArH), 11.70 (s-broad, 1H, N—H).

Anal. Calcd. for C$_{12}$H$_{19}$N$_3$O$_4$S: C, 61.59; H, 4.69; N, 10.26; S, 7.82. Found C, 61.73; H, 4.64; N, 10.28; S, 7.60.

When Compound IVA (2.0 g., 10 mmoles) was refluxed with an excess of benzoyl chloride in ethanol (100 ml.) and triethylamine (2.0 g., 20.0 mmoles) for 10 hours, concentrated and cooled, 1.5 g. (36%) of Compound VIII crystallized. Dropwise addition of ethyl ether to the ethanol concentrate promoted precipitation of the product.

EXAMPLE 22

2-Benzamido-4-benzoyl-5-ethyloxalyl-4H-1,3,4-thiadiazine Oxime Benxoate (Compound IX)

To a suspension of 3.0 g. (6.90 mmoles) of Compound VIC in acetonitrile (100 ml.) and pyridine (3.0 ml.) an excess of benzoyl chloride (10.0 g., 7.20 mmoles) was added. The resulting yellow solution was refluxed for 35 hours. After cooling, the tribenzoylated adduct (Compound IX) separated from solution and was filtered, washed and dried to give 2.0 g. (53%) of the crude white precipitate. After recrystallizing from ethanol, Compound IX melted at 215°–218°; ir (potassium bromide): 3150-3300 (NH), cm$^{-1}$; pmr (hexadeuteriodimethylsulfoxide): δ1.35 (t, 3H, CH$_3$), 4.40 (q, 2H, OCH$_2$.), 8.30-7.30 (m, 16H, ArH, vinyl).

Anal. Calcd. for C$_{28}$H$_{22}$N$_4$O$_6$S: C, 61.97; H, 4.10; N, 10.33; S, 5.90. Found: C, 61.73; H, 4.00; N, 10.12; S, 5.69.

EXAMPLE 23

2-Benzimido-3-benzoyl-5-ethyloxalyl-2,3-dihydro-6H-1,3,4-thiadiazine Oxime Benzoate (Compound VB)

After concentrating the filtrate from the previous experiment (from which Compound IX crystallized) under reduced pressure, 150 ml. of ethyl ether were added and the resulting suspension allowed to sit for 0.5 hour. Solid material was filtered off and the ether filtrate washed with 5% sodium bicarbonate (1×100 ml.) and water (2×150 ml.). The ether was dried (magnesium sulfate), filtered and concentrated under reduced pressure. Slow addition of a petroleum ether-ethanol mixture (1:1) precipitated 1.0 g (27%) of the colorless tribenzoylated adduct Compound VB, m.p. 173°–175° (ethanol, chloroform); ir (potassium bromide): 1770–1710 (C=O), 1625 (C=N) cm$^{-1}$; pmr (deuteriochloroform): δ1.35 (t, 3H, CH$_3$), 4.14 (s, 2H, S—CH$_2$), 4.50 (q, 2H, OCH$_2$), 7.35–7.70 (m, 9H, ArH), 7.85–8.25 (m, 6H, ArH).

Anal. Calcd. for C$_{28}$H$_{22}$N$_4$O$_6$S: C, 61.97; H, 4.10; N, 10.33; S, 5.90. Found: C, 61.76; H, 4.13; N, 10.56; S, 6.16.

EXAMPLE 24

2-Imino-3-amino-4-carbethoxymethylidenethiazolidine (Compound X)

In an ice bath, 3.0 g. (12.7 mmoles) of Compound IIIB hydrochloride dissolved in 60 ml. of distilled water was neutralized with 5% sodium carbonate solution. The aqueous solution was extracted 3 times with ethyl ether (30 ml. portions). The extracts were combined, washed with water, dried (calcium chloride) and evaporated under reduced pressure, leaving a white solid. Free base Compound X (1.4 g., 55%) was obtained after crystallization from isopropanol, and melted at 135°–137°; ir (potassium bromide): 3230 (N—H), 1675 (C=O), 1550–1650 (C=N) cm$^{-1}$; uv, λmax (ethanol): nm (log ε) 290 (25.6); pmr (deuteriochloroform): δ1.27 (t, 3H, CH$_3$), 4.00–4.41 (m, 4H, N—H, OCH$_2$), 4.45–4.55 (m, 3H SCH$_2$, vinyl), 5.75 (s-broad, 1H, =NH).

Anal. Calcd. for C$_7$H$_{11}$N$_3$O$_2$S: C, 41.77; H, 5.52; N, 20.88; S, 15.91. Found: C, 41.42; H, 5.68; N, 20.49; S, 15.72.

EXAMPLE 25

Ethyl 2-Phenylthiazolo[2,3-c]-s-triazole-5-acetate (Compound XI)

Phosphoryl chloride (6.0 ml.) and the 2-(2-benzoylhydrazino)thiazole (Compound IIC) (3.0 g., 10.0 mmoles) were added to 35 ml. of xylene and heated to form a bright orange solution. After refluxing for 8 hours with constant stirring, an insoluble black residue settled to the bottom of the flask. The chilled reaction mixture was diluted with petroleum ether and the liquid then decanted. Sodium bicarbonate solution (10%, 150 ml.) and methylene chloride (60 ml.) dissolved the dark residue, after which the organic layer was separated. Two successive methylene chloride extractions (2×50 ml.) were combined, washed twice with water (2×50 ml.), and dried over magnesium sulfate. After twice treating the methylene chloride solution with Norite, the clear solution was evaporated to yield 0.8 g. (28%) of impure product Compound XI. Pure Compound XI was obtained after several crystallizations from benzene, m.p. 157°–150°; ir (potassium bromide): 1715 (C=O), 1460–1450 (C=N) cm$^{-1}$; pmr (acetone-d6): δ0.85 (t, 3H, CH$_3$), 3.40–3.70 (m, 4H, OCH$_2$, CH$_2$CO), 7.15 (s, 1H, vinyl), 7.45 (s, 5H, ArH).

Anal. Calcd. for C$_{14}$H$_{13}$N$_3$O$_2$S: C, 58.51; H, 4.57; N, 14.63; S, 11.14; m.w., 287. Found: C, 58.26; H, 4.53; N, 14.57; S, 11.15; M+, 287.

EXAMPLE 26

Ethyl 3-Phenylthiazolo[3,2-b]-s-triazole-5-acetate (Compound XII).

3-Phenyl-1,2,4-triazole-5-thiol (Compound XIV) was first prepared by adding 1-benzoyl-3-thiosemicarbizide (3.9 g., 20.0 mmoles) to a solution of sodium (1.5 g.) in ethanol (50 ml.) and refluxed 12 hours. After evaporation to dryness under reduced pressure, the residue was dissolved in water (100 ml.), filtered, and acidified with 10% acetic acid. The precipitate crystallized from water, yielded 2.8 g. of Compound XIV as colorless leaflets (m.p. 254°–256°).

A solution of 3.0 g. (16.9 mmoles) of Compound XIV in 80 ml. of absolute ethanol was stirred while 3.0 g. of triethylamine (17.0 mmoles) and 2.8 g. of ethyl 4-chloroacetoacetate (17.0 mmoles) were added. The clear solution which resulted was refluxed for 12 hours. When cooled, 2.0 g (62%) of Compound XII crystallized, m.p. 131°–133° (ethanol); ir (potassium bromide): 1760 (C=O), 1560–1640 (C=N) cm$^{-1}$; uv, λmax (ethanol): nm (log ε) 268 (20.0); pmr (deuteriochloroform): 1.30 (t, 3H, CH$_3$), 4.25 (s, 2H, CH$_2$CO), 4.40 (q, 2H, OCH$_2$), 7.15 (s, 1H, vinyl), 7.30–7.85 (m, 3H, ArH), 8.03–8.52 (m, 2H, ArH).

Anal. Calcd. for C$_{14}$H$_{13}$O$_2$N$_3$S: C, 58.51; H, 4.57; N, 14.63; S, 11.14; m.w., 287. Found: C, 58.71; H, 4.52; N, 14.41; S, 10.94; M+, 287.

Using a procedure analogous to that used for the preparation of compound XI, 1.0 g. (3.0 mmoles) of the 2-benzimido-3-aminothiazoline (Compound XIII) in dry xylene (20 ml.) and phosphoryl chloride (7 ml.) was refluxed 12 hours. Following the previously described workup, 0.33 g. (37%) of Compound XII, as identified by spectroscopy and m.p., was obtained.

EXAMPLE 27

Ethyl 2-Benzimido-3-aminothiazoline-4-acetate (Compound XIII).

At room temperature, 3.5 g. (30.0 mmoles) of benzoyl chloride was added at once to 6.0 g. (30.0 mmoles) of thiazoline Compound IIIB) hydrochloride syspended in 100 ml. of ethanol and 7.0 g. of triethylamine. After stirring for 2.5 hours (room temperature) the clear yellow solution was refluxed 8 hours, then concentrated to 50 ml. and water slowly added until the white product precipitated. Compound XIII (8.0 g., 87%) was collected, dried and crystallized from 2-propanol as colorless needles melting at 130°–132°; ir (potassium bromide): 3300–2850 (H$_2$N—N), 1725 (C=O), 1550–1500 (C=N, C=O) cm$^{-1}$; pmr deuteriochloroform): δ1.25 (t, 3H,CH$_3$), 3.70 (s, 2H, CH$_2$CO), 4.15 (q, 2H, OCH$_2$), 5.20 (s-broad, 2H, NH$_2$), 6.33 (s, 1H, vinyl), 7.20–7.50 (m, 3H, ArH), 8.15–8.40 (m, 2H, ArH).

Anal. Calcd. for C$_{14}$H$_{15}$N$_3$O$_3$S: C, 55.05; H, 4.96; N, 13.77; S, 10.49. Found: C, 54.92; H, 5.00; N, 13.80; S, 10.26.

EXPERIMENTAL EVALUATIONS

As noted, certain of the compounds of this invention have demonstrated utility as selective herbicides. One study conducted in relation to plant herbicidal activity involved the use of conventional test procedures to determine activity of the test materials as a pre-emergent herbicide applied at a rate of 10 pounds per acre and as a post-emergent herbicide sprayed on plants after they have erupted at a level of 4,000 parts per million. Among the weeds against which these compounds were screened are pigweeds, cotton, crab grass, barnyard grass, wild oats, yellow fox tail, velvet leaf, morning glory, and the like. The results of a screening of certain compounds of this invention are set forth in Table 2, the data being set forth as a "percent control" compared with a control plot on which no herbicide has been employed. Thus, 75% control indicates that only 25% of the number of plants grew (or survived) when the experimental herbicide was applied as compared with the non-herbicide control.

Table 2 gives percent control data for a variety of weeds and a number of the compounds of this invention. As these data reveal, substantial selective herbicidal activity has been illustrated for certain compounds on selected weeds whereas other compounds tested to not show herbicidal activity under the conditions and test procedures employed.

As the foregoing has demonstrated, a number of new compounds have been obtained from the reaction of thiosemicarbazide and 4-chloroacetoacetate under a variety of reaction conditions along with derivatives thereof obtained by benzoylation or nitrozation. A number of these compounds have been shown to exhibit utility as herbicides under certain test procedures.

TABLE 2

HERBICIDAL DATA
PER CENT CONTROL

| TREATMENT | COMPOUND NO. | | | | | | |
|---|---|---|---|---|---|---|---|
| | IA | IB | ID | IIIA | VA | VIA | VIIIB |
| Pre Emergent Application | | | | | | | |
| Pigweeds | 0 | 0 | 0 | 0 | 0 | 0 | 0 |
| Cotton | 0 | 0 | 0 | 0 | 0 | 0 | 0 |
| Crabgrass | 0 | 0 | 0 | 0 | 60 | 0 | 0 |
| Barnyard Grass | 0 | 0 | 0 | 0 | 95 | 0 | 0 |
| Wild Oats | 80 | 0 | 0 | 0 | 0 | 0 | 0 |
| Yellow Foxtail | 0 | 0 | 0 | 0 | 0 | 0 | 0 |
| Velvet Leaf | 0 | 0 | 0 | 0 | 0 | 0 | 0 |
| Morning Glory | 90 | 0 | 0 | 0 | 0 | 0 | 0 |
| Post Emergent Application | | | | | | | |
| Nutsedge | 0 | 0 | 0 | 0 | 30 | 0 | 0 |
| Pigweeds | — | 0 | 0 | 0 | — | — | 0 |
| Cotton | 0 | 0 | 0 | 0 | 0 | 60 | 0 |
| Crabgrass | 0 | 0 | 0 | 0 | 0 | 20 | 0 |
| Barnyard Grass | 0 | 0 | 0 | 0 | 0 | 0 | 0 |
| Wild Oats | 0 | 0 | 0 | 0 | 0 | 0 | 0 |
| Yellow Foxtail | 0 | 0 | 0 | 0 | 0 | 0 | 0 |
| Velvet Leaf | 0 | 0 | 0 | 0 | 0 | 90 | 0 |
| Morning Glory | 0 | 0 | 0 | 0 | 40 | 60 | 0 |

I claim:

1. 2-Amino-5-ethyloxalyl-6H-1,3,4-thiadiazine oxime of the formula (VIA)

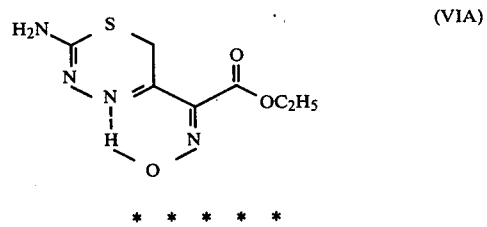

* * * * *

UNITED STATES PATENT AND TRADEMARK OFFICE
CERTIFICATE OF CORRECTION

PATENT NO. : 4,254,259
DATED : March 3, 1981
INVENTOR(S) : Ernest E. Campaigne et al.

It is certified that error appears in the above—identified patent and that said Letters Patent is hereby corrected as shown below:

Column 1, line 24, "gamma" should be -- gamma --

Column 1, line 25, "gamma" should be -- gamma --

Column 1, line 51, "objects  " should be -- objects, --

Column 3, line 39, "b]s" should be -- b]s --

Column 3, line 49, "c]s" should be c]s --

Column 4, line 62 -

" 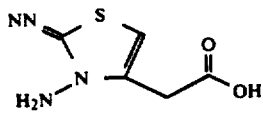 " should be -- 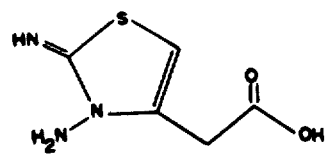 --

UNITED STATES PATENT AND TRADEMARK OFFICE
CERTIFICATE OF CORRECTION

PATENT NO. : 4,254,259  
DATED : March 3, 1981  
INVENTOR(S) : Ernest E. Campaigne; Thomas Selby Page 2 of 3

It is certified that error appears in the above-identified patent and that said Letters Patent are hereby corrected as shown below:

Column 6, line 14, "benzoata" should be -- benzoate --

Column 8, line 31, "c]s" should be --c]s--

Column 8, line 32, "b]s" should be -- b]s --

Column 9, line 41, "analysis" should be -- analyses --

Column 11, line 64, "49,76" should be -- 49.76 --

Column 12, line 60, "11 7" should be -- 11.7 --

Column 13, line 31, "Hydrochloride." should be -- Hydrochloride)--

Column 13, line 66, "N-N+" should be -- N-H+ --

Column 13, line 69 "deuteriochoroform" should be
               -- deuteriochloroform --

Column 14, line 2, "NH)" should be -- NH). --

Column 14, line 62, "(N-H," should be -- (N-H), --

Column 16, line 12, ".w.," should be -- m.w., --

Column 16, line 48, "VIB))." should be -- VIB). --

Column 16, line 61, "(10.0)" (second occurrence) should read
               -- (10.0), --

UNITED STATES PATENT AND TRADEMARK OFFICE
CERTIFICATE OF CORRECTION

PATENT NO. : 4,254,259
DATED : March 3, 1981
INVENTOR(S) : Ernest E. Campaigne et al.

It is certified that error appears in the above—identified patent and that said Letters Patent is hereby corrected as shown below:

Column 18, line 29, "petrolium" should be -- petroleum --

Column 18, line 39, "Found " should be -- Found: --

Column 18, line 51, "Benxoate" should be -- Benzoate --

Column 19, line 42, "3H " should be -- 3H, --

Column 19, line 47, "c]s" should be -- c]s --

Column 20, line 9, "b]s" should be -- b]s --

Column 20, line 36, "compound" should be -- Compound --

Column 20, line 48, "syspended" should be --suspended --

Column 21, line 26, "to" should be -- do --

Signed and Sealed this

Sixteenth Day of June 1981

[SEAL]

Attest:

RENE D. TEGTMEYER

Attesting Officer    Acting Commissioner of Patents and Trademarks